(12) United States Patent
Roser

(10) Patent No.: US 6,224,567 B1
(45) Date of Patent: May 1, 2001

(54) MODIFIED DISPOSABLE INJECTOR DEVICE

(75) Inventor: Bruce Joseph Roser, Cambridge (GB)

(73) Assignee: Cambridge Biostability Limited, Cambridge (GB)

(*) Notice: Subject to any disclaimer, the term of this patent is extended or adjusted under 35 U.S.C. 154(b) by 0 days.

(21) Appl. No.: 09/637,014

(22) Filed: Aug. 14, 2000

Related U.S. Application Data

(63) Continuation-in-part of application No. 09/392,293, filed on Sep. 8, 1999, now Pat. No. 6,102,896.

(51) Int. Cl.⁷ ................................................. A61M 5/30
(52) U.S. Cl. ............................... 604/68; 604/70; 604/218
(58) Field of Search .................. 604/68, 70, 72, 604/140, 141, 152, 218

(56) References Cited

U.S. PATENT DOCUMENTS

| | | | |
|---|---|---|---|
| 3,945,379 | * 3/1976 | Pritz et al. ........................ | 604/70 |
| 5,304,128 | * 4/1994 | Haber et al. ...................... | 604/68 |
| 5,334,144 | * 8/1994 | Alchas et al. .................... | 604/68 |
| 5,938,637 | * 8/1999 | Austin et al. ................. | 604/68 X |
| 6,013,050 | * 1/2000 | Bellhouse et al. ............... | 604/70 |
| 6,096,002 | * 8/2000 | Landau ............................. | 604/68 |
| 6,102,896 | * 8/2000 | Roser .............................. | 604/218 |

* cited by examiner

Primary Examiner—John D. Yasko
(74) Attorney, Agent, or Firm—Jacobson, Price, Holman & Stern, PLLC

(57) ABSTRACT

The present invention is a modified single use hand-operated injector device consisting of a plunger, a base, a snap means for resisting plunger movement and an injection means for injecting parenteral medication through a skin surface of a patient. The improvement comprises a check valve seated in a cannula and a widened receptacle area within a high pressure barrel through which the cannula passes. When the check-valve plug expels upon increase in pressure, into the widened receptacle area the parenteral medication efficiently flows around the plug and into the subcutaneous tissue of the patient.

6 Claims, 2 Drawing Sheets

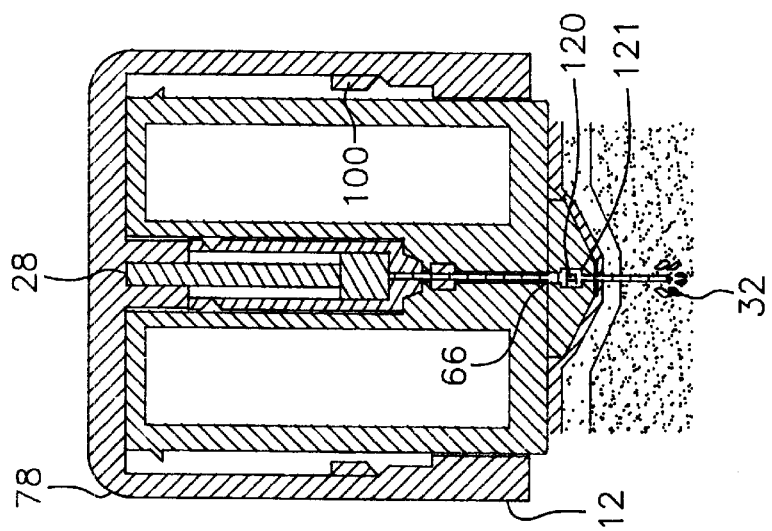
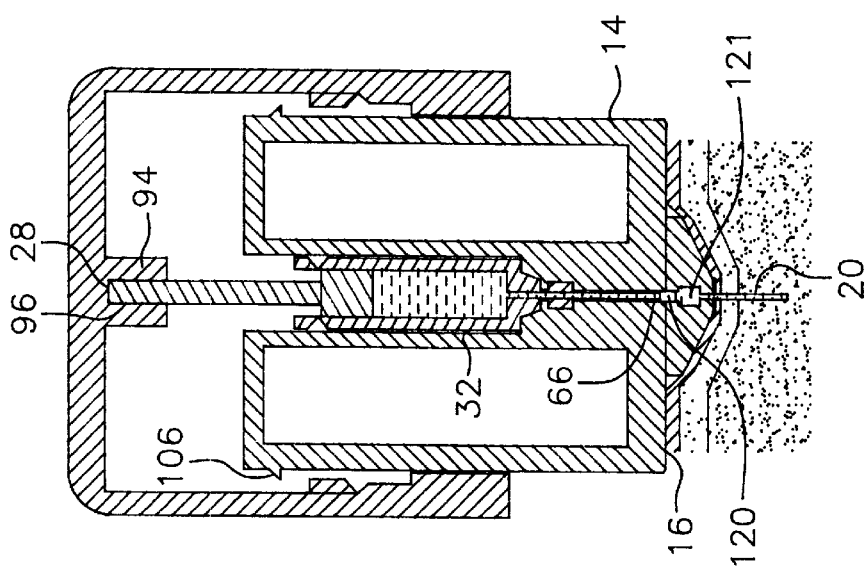
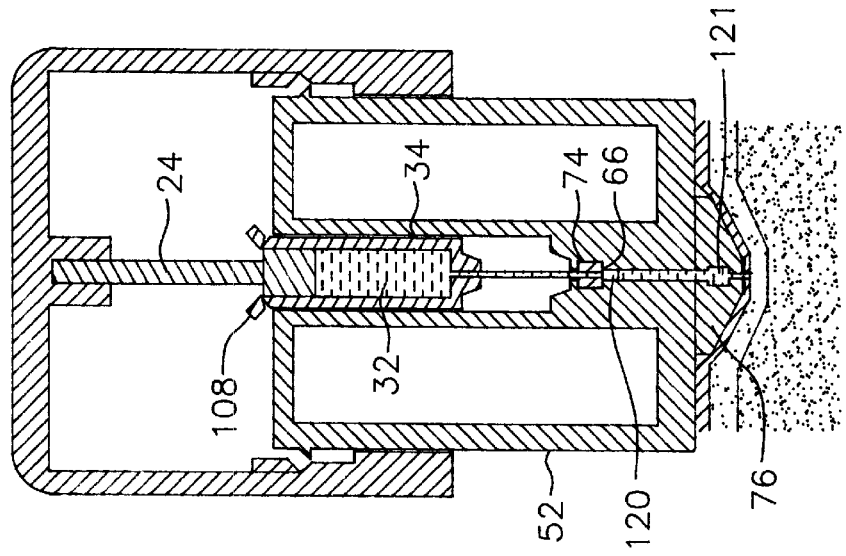

MODIFIED DISPOSABLE INJECTOR DEVICE

RELATED APPLICATION

This application is a continuation-in-part of application Ser. No. 09/392,293, filed Sep. 8, 1999, now U.S. Pat. No. 6,102,896.

BACKGROUND OF THE INVENTION

1. Field of the Invention

This invention relates generally to disposable injector devices and more specifically it concerns a check valve modification to isolate pressure upon administration of medicament through a patient's skin.

2. Description of the Prior Art

In general, a number of problems and risks have been associated with the parenteral injection for at least a century. For instance, the use of a standard hollow metal needle attached to a syringe requires thirteen steps and creates health risks not only for the patient, but the medical personnel as well.

This process can only be administered by adequately trained medical personnel. The risks of incorrect dilution or dose measurement are apparent. Any failure of sterile technique may lead to infection, ultimately presenting a greater risk to the patient. The final injection step requires training and practice to achieve the correct depth and dexterity in order to deliver the injection quickly and with minimal pain. Due to the lack of trained personnel, this is a major obstacle to successful immunization campaigns.

Advancements have, in fact occurred. Today, most syringes and needles are disposable, however, such disposable syringes are routinely re-used in developing countries and by people who suffer from drug addiction. Because of this re-use, infections such as hepatitis and AIDS are at a higher risk of transmission.

Furthermore, few drugs or vaccines are injection-ready stable liquids, rather the great majority of parenteral preparations are freeze-dried, thus requiring dilution before injection and constant refrigeration during storage.

Finally, patient compliance and compliance with the leading health organizations are at issue and numerous difficulties must be conquered. When standard syringes and needles are used, patients often do not return to field stations for follow-up doses. For instance, infants, who require a series of injections, fail to return due to the pain and anxiety a needle creates. Present parenteral injection technology, the World Health Organization (WHO) claims, is incompatible with requirements for the planned Global Programme of Vaccination and Immunization (GPV) initiatives.

An estimated six additional parenteral vaccines will be recommended for childhood vaccination by the year 2005, requiring a total of 3.6 billion immunization injections per year. The total number of parenteral injections, including injected drugs as well as vaccines, will be roughly ten times this number. Major health care providers such as UNICEF, the WHO and CDC have recently confirmed the requirement of a radical new technology that can be used by personnel with minimal training and that is safer, more convenient, and more comfortable than the syringe and needle. (Jodar L., Aguado T., and Lambert P-H, (1998) Revolutionizing Immunizations *Gen. Eng. News,* 18, p. 6.) Criteria include: heat stability, no cold chain of refrigerators; affordable; zero risk of cross infection; individual injection devices and vaccine doses packaged together; simple and easy to use; easy and safe disposal; no wastage; minimal discomfort, and minimum volume.

Some delivery devices address these criteria. It is known to package parenteral medications in disposable, single dose delivery devices. One approach is the packaging of single doses of vaccines in simple plastic blisters or collapsible tubes with an integral hypodermic needle attached. (U.S. Pat. Nos. 4,013,073 and 4,018,222). The Uniject™ plastic blister device (Becton Dickinson and Co.) is another example. Known single-use injectors require medical expertise, however, and the naked needle is a drawback.

Certain single-use injectors self-destruct, thereby eliminating the temptation to re-use. Examples are disclosed in U.S. Pat. No. 3,998,224 to Chiquiar-Arias, U.S. Pat. No. 4,233,975 to Yerman, and U.S. Pat. No. 4,391,272 to Staempfli. Another example is the Soloshot™ syringe (manufactured by Becton Dickinson). However, drawbacks include the price, which is more expensive than a standard syringe, and the requirement of medical personnel to effectively use such a device.

Further improvements include breakable tabs and snap rings in plastic container, such as bottles, in order to prevent tampering and ensure sealing. An early example is disclosed in U.S. Pat. No. 3,407,956 to Linkletter, which shows a removable and replaceable bottle cap. The plastic cap possesses an annular bead molded to the inside, which overrides a similar bead molded on the outside of the neck of the bottle. Natural elasticity of the materials used in manufacturing the cap permit it to expand temporarily, allowing the beads to override and then to contract again immediately once the beads have passed each other. This seats the cap firmly on the container, thereby providing an effective seal.

Needleless injectors exist now as well. These injectors use a fine stream of pressurized liquid to penetrate the skin. Pain is considerably less than that experienced during a conventional injection. Early designs used high pressure throughout the injection, to punch a hole through the tough epidermis. However, the bulk of the injection could then be infused along the initial track under much lower pressure. U.S. Pat. No. 2,704,542 to Scherer and U.S. Pat. No. 3,908,651 to Fudge disclose examples of this design. Ultimately, the engineering demands of changing the pressure during the injection and resulting complexity have limited the use of such devices.

Standard high-pressure needleless jet injectors are also inherently complex, requiring precision engineering of a number of machined steel parts. Most of the designs focus on the production of robust, reliable, heavy-duty machines capable of many injections at high rates for mass immunization campaigns. See Ismach U.S. Pat. No. 3,057,349 (1959), Landau U.S. Pat. No. 4,266,541 (1981), U.S. Pat. No. 5,746,714 (1998), D'Antonio et al PCT patent WO98/17332 (1998), Parsons PCT patent WO98/15307 (1998). Infection due to cross-contamination in such jet injectors occurs, most likely due to the high pressure in the tissue. As the tissue is distended by the injection and the pressure simultaneously falls in the injector, the injector sucks the liquid which may be contaminated with blood or interstitial fluid. The development of single-use vials which insert into the jet injector addresses this problem. Such an approach may be combined with a replaceable nozzle and a vaccine fluid path of cheap plastic, as disclosed in U.S. Pat. No. 4,266,541 to Landau.

Developed under the trademark "Intraject", a mono-dose disposable jet injector by Weston Medical, UK, this injector uses a highly compressed gas in a cannister to propel the vaccine dose. See Lloyd J. S., Aguado M. T., Pre-Filled Monodose Injection Devices: A safety standard for new vaccines, or a revolution in the delivery of immunizations?, Global Programme on Vaccines and Immunization, World Health Organization, May, 1998.

It is known that extraordinary stability can be conferred on very labile biomolecules by drying them in glasses formed from certain sugars. Trehalose is one example. See U.S. Pat. No. 4,891,319 to Roser, and Colaco C., Sen S., Thangavelu M., Pinder S., and Roser, B. J., Extraordinary stability of enzymes dried in trehalose: Simplified molecular biology. *Biotechnol.* 10 1007–1011 (1992). A similar technique can be applied to stabilized vaccines. See Gribbon E. M., Sen S., Roser B. J. and Kampinga J., Stabilization of Vaccines Using Trehalose (Q-T4) Technology, in F. Brown, (ed) New Approaches to Stabilization of Vaccine Potency *Dev Biol Stand* Basel Karger 87 193–199-(1996).

More recently, glass-forming preparations utilizing sugar derivatives includes the development of stabilization brought about by the active biomolecules remaining in solid solution in the "solid solvent" phase of the glass matrix. The biomolecules remain stable due to the high viscosity of the inert glass. In these solid solutions, molecular diffusion and molecular motion are negligible. Chemical reactions, which depend on the reactive species being free to diffuse together, are non-existent. Providing the glass itself is chemically non-reactive and dry, the product typically remains stable at temperatures up to the softening point of the glass, often expressed as the "glass-transition temperature" or Tg. Molecular diffusion and degregation commence only upon the softening and melting of the glass. Even at temperatures above the Tg, damage will only occur after a certain period of time. Because degradation reactions are chemical processes with typical kinetics, the factor determining product damage is a mathematical product of the elevated temperature and the time of exposure rather than just the high temperature. Even fragile compounds in these glasses may be briefly exposed to high temperatures with insignificant damage. While the sugar glass formulations have advantages in stability over conventional parenteral preparations, other difficulties of conventional parenteral injection remain, such as dose mismeasurement, pain, and infection risk.

Also suitable for stabilization of parenteral medications (See U.S. Pat. No. 4,698,318), the phosphate glasses are typically much stronger than sugar glasses and because of this strength, phosphate glasses are often used as structural elements in bone repair. Mixtures of metal carboxylates such as the acetate salts of sodium, potassium, calcium and zinc also form excellent glasses, PCT Publication No WO90/11756. Through the use of different mixtures of individual carboxylates and different metal cations, it is possible to tailor these phosphate and carboxylate glasses to dissolve at different, specific rates in body fluids. Composed of simple chemicals normally present in the body, phosphate and carboxylate glasses exhibit low toxicity. However, a major disadvantage exists in that a high temperature is necessary to melt them. Because of this high temperature, most drugs are precluded from being incorporated in the glass in solid solution, and ultimately, their use is restricted to preformed hollow tubes which are loaded with stable powdered drugs. See U.S. Pat. Nos. 4,793,997 and 4,866,097. A difficulty exists in filling narrow tubes with dry powders, therefore, phosphate glass tubes are of large diameter. Large diameter tubes create more physical trauma upon injection, and therefore are suitable only for veterinary applications.

Several approaches address the problem of filling narrow tubes with powdered actives. The powdered drug may be suspended in a non-aqueous liquid in which it is insoluble. These suspensions flow more readily into fine capillary tubes and carry the powdered active with them. Many organic solvents such as ethanol, acetone, dichloromethane, chloroform, and toluene may be used. However, many of these industrial solvents react destructively with biological molecules. By first enclosing the actives in stabilizing sugar glasses, as disclosed in U.S. Pat. No. 5,589,167 and in Gribbon E., Hatley R., Gard T., Blair J., Kampinga J. and Roser B. Q-T4 Stabilisation and novel drug delivery formats, Conf. Report Amer. Assoc. Pharm. Soc., 10th annual meeting, Miami Beach, Fla. (1995), this difficulty is overcome.

Truly disposable liquid jet injectors have previously been developed that operate on the new principle of using only the modest pressure of the human hand to generate a brief pulse of high pressure. This brief pressure punches a narrow hole through the skin to allow the subsequent delivery of the bulk of the dose at lower pressure (Roser, B. Disposable Injector Device U.S. Pat. No. 6,102,896. These designs for a disposable liquid jet injector, however still suffer major disadvantages. Both the reservoir assembly and the injector itself need sterile manufacture and assembly into the final device. Further, the liquid reservoir and the injector device need engineering to withstand high pressure pulses. Additionally, the completion of the power stroke is completely dependent upon the maintenance of hand pressure until the full dose of liquid has been delivered.

The power derived from steady pressure from the hand, which converts to a sharp pulse of high pressure, follows the structural breaking of "snap tabs" or the sudden overcoming of the resistance of "snap rings." The liquid dose to be injected is located in a centrally located reservoir and the high pressure barrel is located in the base of the injector itself which also has the injection orifice in the base. The existing design generates instantaneous high pressure in the bore from the breaking of the "snap tabs" and the beginning of the movement of the tubular shaft in the bore is transmitted equally and undiminished in all directions throughout the fluid. This creates a pressure of approximately 5,000 psi generated in the bore to be simultaneously applied to the first end of the plunger.

This pressure, applied over a much larger cross sectional area than that of the bore, applies a greater force resisting the downward movement of the plunger. This force is of the order of 25 times that generated in the bore since the diameter of the plunger is five times that of the bore. Enormous resistance to continued movement is generated and ultimately stops the downward motion of the plunger. This defeats the purpose of the injector by arresting the power stroke. The subject of the present invention eliminates this problem.

SUMMARY OF THE INVENTION

The present invention, a modified disposable liquid injector complete with a check valve to isolate pressure overcomes the above described difficulties and drawbacks of the prior art.

A check valve is placed at the tip of the tubular shaft to isolate the pressure in the bore. The check valve in its simplest form is a plug which is a press fit in the free end of the tubular shaft. A shoulder on the plug sits against the butt end of the tubular shaft and seals it against any flow of liquid or the transmission of the high pressure in the bore backward into the reservoir. This allows the tubular shaft to travel to the bottom of the bore, where the pressure in the bore would suddenly drop due to the arrest of the downward movement of the reservoir by contact of the first end of the reservoir barrel with the nozzle end of the tubular cavity.

The plunger begins to move in the reservoir barrel which causes the check valve to open by expelling the plug due to the increase of pressure in the reservoir barrel. The reservoir liquid subsequently flows through the tubular shaft as described before. The narrow bore is modified to accommodate the check valve plug when it is expelled from the free end of the tubular shaft when the plunger "bottoms out." The present invention with its check valve modification ensures a precise delivery of the medication by effectively isolating and redistributing the pressure.

BRIEF DESCRIPTION OF THE DRAWINGS

Several embodiments of the invention are illustrated and described in the accompanying drawings, forming a part of the specification, wherein:

FIGS. 2A, 2B, and 2C are cross-sectional view of an injector device having jet injection means, showing in succession the breaking of the break tabs and contained liquid accelerated towards the nozzle, the formation of the liquid jet which punches a fine hole through the epidermis and dermis and the completed injection with the liquid contents of the reservoir barrel flowing around the dislodged check valve in the widened receptacle.

DETAILED DESCRIPTION OF THE PREFERRED EMBODIMENTS

Figure 1:
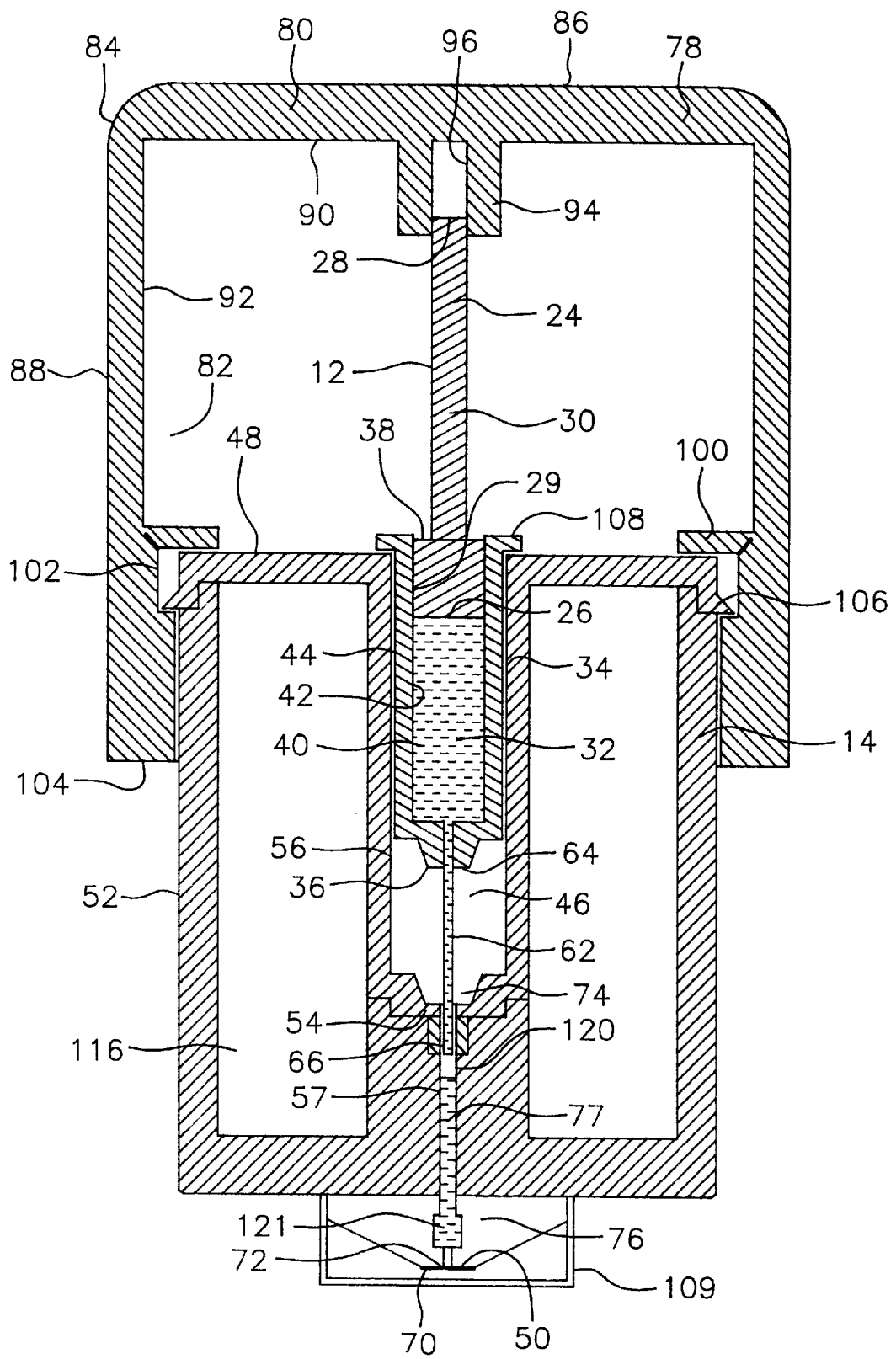
FIG. 1 is a cross-sectional view of an injector device in the initial position, the injector device having jet injection and a plunger which is struck by a cap after the snap point is reached, creating pressure which is modified by the presence of a check valve.

As can be seen in FIG. 1, the device consists of a cylindrical cap 78 held in place on a base 14, which is generally tubular, by a combination of several breakable restraining tabs 100 located circumferentially around the inside of the cap 78. The force at which these tabs fail can be varied over a wide range but is ideally close to 30 Newtons or the force equivalent to a weight of about 3 Kg (6.6 lbs).

The cap is retained in the other direction by a ramp-shaped retaining ring 106. The cap 78 may have a central section 80. The central section 80 is generally planar and is preferably either flat or slightly convex. The central section has a periphery 84. A peripheral section 82 of the cap is attached to the periphery 84 of the central section 80. The peripheral section of the cap extends approximately perpendicular to the central section and toward the skin surface 16 of a patient. Each of the central and peripheral sections has an outer surface 86 or 88 and an inner surface 90 or 92 respectively. The hand force is applied to the central section 80 of the cap 78, with the force vector being toward the skin surface. The inner surface 92 of the peripheral section of the cap contacts the outer surface 52 of the base. The moving portion of the plunger section 12 includes the cap. The cap may have one or more grooves 102 between the cap break tabs and the free end of the peripheral section 104.

The base has a plunger end 48, a nozzle end 50, and an outer surface 52. The base is at least partially composed of plastic, and preferably entirely composed of plastic.

The cavity 46 of the base has a nozzle end 54 and a cavity surface 56. The longitudinal axis of the cavity 46 is coincident with the longitudinal axis of the plunger. The plunger 24 is located at least partially within the cavity. The plunger slides within the cavity parallel to the longitudinal axis of the cavity. If a barrel is used, the barrel is located between the plunger 24 and the cavity surface 56. Preferably the base includes a bore 57, of smaller diameter than the cavity, extending between the nozzle end 54 of the cavity and the nozzle end 50 of the base. The base 14 has a peripheral space 116 between the cavity and the outer surface of the base. A sealing membrane 70 covers the nozzle end 50 of the base.

The base also has an integral tapered nozzle 76 containing a fine orifice. The nozzle forms a pressure seal when the base of the device is pressed against the skin. A cylindrical cavity 46 in the base houses and supports a reservoir barrel 34 that has a sliding fit in the cavity 46. Several thin collapsible secondary break-tabs 108 with a yield force much lower than the restraining tabs 100 locate the reservoir barrel at the top of the cylindrical cavity 46.

The plunger section 12 includes a cannula 62. The cannula is preferably cylindrical, with a circular cross-section. The cannula 62 has an attachment end 64 and a free end 66. The free end 66 of the cannula 62 is located within the bore 57 when the plunger section 12 is in the initial position. The nozzle end 72 of the bore 57 is sealed by a sealing membrane 70. The cannula 62 extends from the base of the reservoir barrel 34 and is a snug fit in a fine-bore high-pressure barrel 57 through the base and nozzle. Optionally a section of elastomeric tubing such as silicone, neoprene or butyl rubber forms a pressure-tight sliding seal 74 around the cannula 62.

One end of the plunger 24 is held loosely by a retaining ring 94 with an inner surface 96 integral with the cap and is a snug liquid-tight fit in the reservoir barrel, containing the liquid 32 to be injected, which is the same liquid as fills the cannula and the fine-bore high-pressure barrel. This liquid is retained within the device by a sealing membrane 70 over the end of the nozzle. The plunger 24 has a first end 26 and a second end 28. The first end has a periphery 29. To save weight and materials, the plunger may have a central section 30 which is narrower than the first end 26. When at least a part of the parenteral medication is a liquid medication 32 contained in a reservoir means, the first end 26 of the plunger is the end which contacts the medication in the reservoir means.

The plunger section 12 may include a barrel 34. The barrel 34 is tubular and preferably has a circular cross-section. The barrel 34 has a first end 36 and a second end 38. The first end 36 is at least partially closed, so that the barrel is cup-shaped. The barrel 34 has a reservoir 40 adapted to contain the liquid medication 32. The longitudinal axis of the barrel is coincident with the longitudinal axis of the plunger 24. The barrel has an inner surface 42 and an outer surface 44. The barrel 34 is located at least partially within the cavity 46 of the base 14.

A check valve consisting of a snug fitting plug 120 is seated at the free end 66 of the cannula 62 with a shoulder acting as a seal against the butt-end of the cannula. Near the nozzle end of the high-pressure barrel 57, there is a widened area 121 of the barrel bore which acts as a receptacle to house the check valve plug when it is expelled towards the end of the high-pressure phase of the power stroke. The device is pre-loaded with the sterile liquid in a factory. This can be a conventional liquid formulation of a drug or vaccine, which would require that the device be refrigerated. Preferably, a stable non-aqueous ready-to-inject liquid suspension as described in Roser et al U.S. patent application Ser. No. 09/271,204 can be used so that no refrigeration is required. During storage the nozzle is covered by a sterile cap 109, which is removed just prior to use.

Three distinct stages of the injection can be identified in FIGS. 2A–C. The device is pressed against the skin by hand-pressure which is applied to the cap until the breakable primary restraining tabs 100 suddenly yield. The cap 78 accelerates toward the nozzle 76 and strikes the top 28 of the plunger 24. This causes the secondary break-tabs 108 to give way resulting in a rapid instantaneous rise in pressure in the liquid 32 in the reservoir barrel 34 and a 25 fold higher pressure in the liquid column in the high-pressure barrel 77 below the check valve 120. This pressure differential is the result of the cross-sectional area to which the force of the hand pressure is applied in the reservoir barrel being 25 times greater (diameter 0.5 cm) than the cross-sectional area of the end of the cannula in the high-pressure barrel 77 (diameter 1 mm). The central section 30 of the plunger 24, reservoir-barrel 40 and cannula 62 together with the contained liquid 32, are then accelerated en bloc toward the nozzle 76. With a 1 mm diameter fine-bore barrel, the pressure on the liquid in the high-pressure barrel 77 at this stage reaches about 5,000 psi.

The plunger, barrel and cannula, continuing to move en bloc, and drive the small column of liquid, which occupies that part of the high-pressure barrel 77 below the check valve plug 120 in the cannula, through the nozzle 76. This high-pressure jet 20 punches a fine hole, first through the nozzle membrane 70 then through the epidermis and dermis into the loose subcutaneous (SC) tissue. The cannula is stopped from further movement when a first end 36 of the reservoir barrel 34 strikes the nozzle end 54 of the cylindrical cavity 46. This abruptly brings to an end the high-pressure phase of the injection, which therefore lasts only a small fraction of a second. The pressure remaining on the liquid 32 in the reservoir barrel then dislodges the check valve plug 120 from the end of the cannula into the widened area or receptacle 121 at the nozzle end of the high-pressure barrel 57.

With the reservoir barrel arrested, the plunger continues to move inside the reservoir barrel to inject the bulk of the dose of liquid 32. The pressure in the liquid falls to approximately 200 psi. The liquid contents of the reservoir barrel flow around the dislodged check valve 120 in the widened receptacle 121, see FIG. 2C, of the high-pressure barrel 77, through the nozzle 76 and along the track in the epidermal and sub-dermal tissue created by the initial jet of high-pressure liquid 20 and into the subcutaneous tissue. The whole injection is complete in less than a second.

Although specific embodiments of the invention are herein disclosed for purposes of explanation, various modifications thereof, after study of this specification, will be apparent to those skilled in the art to which the invention pertains.

What is claimed is:

1. A single use hand-operated injector device consisting of a plunger section, a base having a cavity and outer surface, a cannula extending from the base and sized to fit into a high-pressure barrel, a snap means for resisting movement of the plunger section and an injection means for injecting at least one parenteral medication through a skin surface of a patient, wherein the improvement comprises:

providing a check valve consisting of a snug fitting plug seated at the free end of the cannula and;

a widened receptacle area at the distal end of the high-pressure barrel through which the cannula passes and which houses the check-valve plug upon expulsion due to the increase of pressure;

whereby, the parenteral medication efficiently flows around the check valve dislodged into the receptacle area at the end of the high-pressure phase of the power stroke and the medication thereby flows into subcutaneous tissue of the patient.

2. The injector device as claimed in claim 1, wherein said check valve plug moves due to an increase in pressure when said plunger section moves into a reservoir barrel whereby the medicament subsequently flows through said cannula.

3. The injector device as claimed in claim 2, wherein said check valve plug has a shoulder which abuts one end of said cannula so as to seal against flow of medicament backward into the reservoir barrel.

4. The injector device as claimed in claim 1, wherein said injector device is pre-loaded with sterile liquid formulation.

5. The injector device as claimed in claim 4, wherein said liquid formulation is a drug or vaccine.

6. The injector device as claimed in claim 5, wherein said vaccine is a stable non-aqueous liquid suspension.

* * * * *